(12) United States Patent
Janssen et al.

(10) Patent No.: US 7,495,142 B2
(45) Date of Patent: Feb. 24, 2009

(54) PROTECTING CATALYTIC SITES OF METALLOALUMINOPHOSPHATE MOLECULAR SIEVES

(75) Inventors: Marcel Johannes Janssen, Kessel-Lo (BE); Luc Roger Marc Martens, Meise (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 138 days.

(21) Appl. No.: 11/818,496

(22) Filed: Jun. 14, 2007

(65) Prior Publication Data

US 2008/0033226 A1 Feb. 7, 2008

Related U.S. Application Data

(62) Division of application No. 10/704,741, filed on Nov. 10, 2003, now Pat. No. 7,241,716.

(51) Int. Cl.
*C07C 1/00* (2006.01)

(52) U.S. Cl. ...................................... 585/640; 585/639
(58) Field of Classification Search .......... 585/639–640
See application file for complete search history.

(56) References Cited

U.S. PATENT DOCUMENTS 6,316,683 B1 * 11/2001 Janssen et al. ............... 585/640
6,455,748 B2 * 9/2002 Janssen et al. ............... 585/638
6,498,120 B1 * 12/2002 Janssen et al. ................ 502/22

\* cited by examiner

*Primary Examiner*—In Suk Bullock

(57) ABSTRACT

Metalloaluminophosphate molecular sieves and metalloaluminophosphate molecular sieve catalyst particles are protecting from degradation by water by maintaining said molecular sieves or catalysts in contact with a liquid mixture of alcohol and water, the mixture of alcohol and water containing from 45 wt % to 99.8 wt % alcohol. The metalloaluminophosphate molecular sieves and metalloaluminophosphate molecular sieve catalyst particles which have been protected in such fashion catalyze the conversion of feedstocks to hydrocarbons.

22 Claims, No Drawings

PROTECTING CATALYTIC SITES OF METALLOALUMINOPHOSPHATE MOLECULAR SIEVES

This application is a divisional of U.S. patent application Ser. No. 10/704,741, now U.S. Pat. No. 7,241,716, filed Nov. 10, 2003, which is fully incorporated herein by reference.

FIELD OF THE INVENTION

This invention relates to a method of stabilizing metalloaluminophosphate molecular sieves during storage and handling, to stabilized metalloaluminophosphate molecular sieves and stabilized metalloaluminophosphate molecular sieve containing catalysts and to the use of these stabilized molecular sieves or catalysts in adsorption and conversion processes.

BACKGROUND OF THE INVENTION

Olefins are traditionally produced from petroleum feedstock by catalytic or steam cracking processes. These cracking processes, especially steam cracking, produce light olefin(s) such as ethylene and/or propylene from a variety of hydrocarbon feedstock. It has been known for some time that oxygenates, especially alcohols, are convertible into light olefin(s). Methanol, the preferred alcohol for light olefin production, is typically synthesized from the catalytic reaction of hydrogen, carbon monoxide and/or carbon dioxide in a methanol reactor in the presence of a heterogeneous catalyst. The preferred methanol conversion process is generally referred to as a methanol-to-olefin(s) process, where methanol is converted to primarily ethylene and/or propylene in the presence of a molecular sieve.

Some of the most useful molecular sieves for converting methanol to olefin(s) are the metalloaluminophosphates such as the silicoaluminophosphates (SAPO's) and the aluminophosphates (ALPO's). SAPO synthesis is described in U.S. Pat. No. 4,440,871, which is herein fully incorporated by reference. SAPO is generally synthesized by the hydrothermal crystallization of a reaction mixture of silicon-, aluminum- and phosphorus-sources and at least one templating agent. Synthesis of a SAPO molecular sieve, its formulation into a SAPO catalyst, and its use in converting a hydrocarbon feedstock into olefin(s), particularly where the feedstock is methanol, is shown in U.S. Pat. Nos. 4,499,327; 4,677,242; 4,677,243; 4,873,390; 5,095,163; 5,714,662 and 6,166,282, all of which are herein fully incorporated by reference.

Metalloaluminophosphate molecular sieves contain a pore system, which is a network of uniform pores and empty cavities. These pores and cavities catch molecules that have a size equal to or less than the size of the pores and cavities, and repel molecules of a larger size.

The pores and cavities of molecular sieves are formed as a result of adding template materials during the molecular sieve manufacturing process. During the formation of the molecular sieves themselves, a lattice type chemical structure forms around the template material, with the template material acting as a means of forming the pore structure within the molecular sieve. The resulting molecular sieve may be combined with other components for the benefit of adjusting various properties of the molecular sieve or to form larger particles.

To make the molecular sieve suitable for use, the template must be at least partially, preferably completely, removed so that the pores and cavities are open to catch molecules, either for the purpose of adsorbing the molecules from the environment or to react the molecules to form a desired product. The reaction occurs when the molecules come into contact with catalytic sites located within the pore system, particularly within one or more of the empty cavities or cages as sometimes called.

The template is conventionally removed from the molecular sieve by calcining or burning out the template. An elution process can also be used to remove the template, although calcination is preferred. Once the template is removed, the molecular sieve is considered to be activated or ready for use. The activated molecular sieve has its pore system, including the empty cavities or cages open to the immediate environment, and ready for use.

Activated metalloaluminophosphate molecular sieves that have catalytic sites within their microporous structure, e.g., silicoaluminophosphate (SAPO) molecular sieves, have been found to be sensitive to moisture. In general, significant exposure of the activated molecular sieves to moisture has been found to deactivate the catalytic activity of the molecular sieves. Unfortunately, methods of protecting activated metalloaluminophosphate molecular sieves against the harmful effects of moisture are limited.

U.S. Pat. No. 6,316,683 (Janssen et al.) discloses a method of protecting catalytic activity of a SAPO molecular sieve by shielding the internal active sites of the molecular sieve from contact with moisture. The template itself can serve as the shield, or an anhydrous blanket can serve as a shield for an activated sieve that does not include template. The anhydrous blanket can be a liquid or a gas under standard temperature and pressure conditions, and does not react to any significant degree with the molecular sieve structure under ambient conditions. In the case of an anhydrous liquid blanket, the liquid contains less than about 200 ppm water, preferably less than about 100 ppm water, more preferably less than about 50 ppm water. The anhydrous liquid is preferably selected from the group consisting of alkanes, cyclo-alkanes, $C_6$-$C_{30}$ aromatics, alcohols, particularly $C_4^+$ branched alcohols. It is desirable to shield the active sites, because activated SAPO molecular sieves will exhibit a loss of catalytic activity when exposed to moisture.

U.S. Pat. No. 4,764,269 (Edwards et al.) discloses a method of protecting SAPO-37 catalyst from deactivating as a result of contact with moisture. The catalyst is maintained under storage conditions such that the organic template component of the molecular sieve is retained in the SAPO-37 molecular sieve, until such time as the catalyst is placed into a catalytic cracking unit. When the catalyst is exposed to the FCC reaction conditions, wherein the reactor is operated at 400° C. to 600° C. and the regenerator operated at about 600° C. to 850° C., the organic template is removed from the molecular sieve pore structure, and the catalyst becomes activated for the cracking of hydrocarbons. According to this procedure, there is little if any contact with moisture.

U.S. Pat. No. 6,395,674 to Fung et. al. discloses a method for addressing the problems relating to protecting molecular sieves from damage due to contact with moisture and damage due to physical contact. The method requires the heat treatment of a molecular sieve containing a template under conditions effective to remove a portion of the template from the microporous structure and cooling the heated molecular sieve to leave an amount of template or degradation product thereof effective to cover catalytic sites within the microporous structure.

U.S. Pat. Nos. 6,225,254; 6,448,460; 6,503,863 to Janssen et. al. disclose a method for preserving the catalytic activity of silicoaluminophosphate molecular sieves which comprises heating template-containing silicoaluminophosphate in an oxygen depleted environment under conditions effective to provide an integrated catalyst life which is greater than that obtained using a non-oxygen depleted environment.

U.S. Pat. No. 6,498,120 (Janssen et al.) discloses a method of rejuvenating a molecular sieve with anhydrous liquid or vapor, until the methanol uptake index is increased by at least 10%. In the examples, this document discloses rejuvenation of a SAPO molecular sieve using liquid methanol in admixture with less than 30 wt % water.

U.S. patent application Ser. No. 10/295,994, published 7 Aug. 2003 under No. 2003/0149321 (Mees et al.) and Mees et al., "Improvement of the Hydrothermal Stability of SAPO-34," Chem. Commun., 2003, (1), 44-45, first published electronically on the web Nov. 22, 2002, discloses a method of protecting SAPO-34 molecular sieve, based on a reversible reaction of $NH_3$ with acid sites of the sieve. The method transforms a $H^+$-SAPO-34 into an $NH_4^+$-SAPO-34 in a reversible way. Once they have undergone this treatment, activated metalloaluminophosphate molecular sieves are protected against degradation by water or steam.

U.S. application Ser. No. 10/113,678, published 2 Jan. 2003 under No. 2003/0004056 (Mees et al.), relates to a method of treating at least one activated metalloaluminophosphate molecular sieve with one or more nitrogen containing compounds selected from the group consisting of amines, monocyclic heterocyclic compounds, organonitrile compounds and mixtures thereof under conditions to chemisorb and/or physisorb the nitrogen-containing compound with the metalloaluminophosphate molecular sieve. Once they have undergone this treatment, activated metalloaluminophosphate molecular sieves are protected against degradation by water or steam.

As seen from the disclosures described herein, many metalloaluminophosphate molecular sieves will exhibit a shortened catalytic life when exposed to a moisture-containing environment. This loss of catalytic life, which is due to a loss in the number of acid catalytic sites, can occur over a very short period of time. This loss of catalytic life is sometimes reversible, but if loss of catalytic activity is too severe, it cannot be restored. In addition there may be irreversible loss of molecular sieve crystallinity and porosity on aging during storage and handling after manufacture.

As new large scale, commercial production facilities, which use metalloaluminophosphate molecular sieves in the production process, continue to be implemented, protecting the activated metalloaluminophosphate molecular sieves from loss of catalytic activity as a result of contact with moisture continues to become an even greater challenge. The present invention provides a new method of protecting the catalytic sites of activated metalloaluminophosphate molecular sieves or catalysts containing metalloaluminophosphate molecular sieves during molecular sieve storage and/or handling or during catalyst storage and/or handling.

SUMMARY OF THE INVENTION

In a first embodiment, the present invention relates to a method of aging an activated metalloaluminophosphate molecular sieve, wherein said activated metalloaluminophosphate molecular sieve is maintained in contact with a liquid mixture of alcohol and water, the mixture of alcohol and water containing from 45 wt % to 99.8 wt % alcohol.

In a second embodiment, the present invention relates to a method for converting a feedstock into a hydrocarbon product in which a metalloaluminophosphate molecular sieve having a methanol adsorption index of at least 0.15 is contacted with an oxygenated feedstock under oxygenate to olefins conversion conditions, wherein, prior to contacting said feedstock, said metalloaluminophosphate molecular sieve has been aged in activated form while in contact with a liquid mixture of alcohol and water, the mixture of alcohol and water containing from 45 wt % to 99.8 wt % alcohol.

In a third embodiment, the present invention relates to a method of aging a used catalyst composition, which method comprises the step of maintaining the used catalyst composition in contact with a liquid mixture of alcohol and water, wherein the mixture of alcohol and water contains from 45 wt % to 99.8 wt % alcohol.

In a fourth embodiment, the present invention relates to a process for the manufacture of metalloaluminophosphate molecular sieve catalyst particles, the process comprising the steps of:
  a) combining a metalloaluminophosphate molecular sieve, a binder and a liquid medium, the liquid medium consisting of a mixture of alcohol and water, wherein the mixture of alcohol and water contains from 45 wt % to 99.8 wt % alcohol; and
  b) forming metalloaluminophosphate molecular sieve catalyst particles.

In a fifth embodiment, the present invention relates to a slurry of metalloaluminophosphate molecular sieve in a liquid medium, wherein the liquid medium consists of a mixture of alcohol and water, wherein the mixture of alcohol and water contains from 45 wt % to 99.8 wt % alcohol.

In a sixth embodiment, the present invention relates to a slurry of metalloaluminophosphate molecular sieve catalyst particles in a liquid medium, wherein the liquid medium consists of a mixture of alcohol and water, wherein the mixture of alcohol and water contains from 45 wt % to 99.8 wt % alcohol.

In preferred aspect of each of these embodiments, the metalloaluminophosphate molecular sieves or metalloaluminophosphate molecular sieve catalyst particles are maintained with a mixture of alcohol and water containing from 50 wt % to 99.5 wt % alcohol, more preferably from 55 wt % to 99 wt % alcohol. In another preferred aspect of each of these embodiments, the mixture of alcohol and water contains from 0.2 wt % to 55 wt % water, more preferably from 0.5 wt % to 50 wt % water.

In each of these embodiments, the alcohol in said alcohol and water mixture is preferably selected from the group consisting of alkyl alcohols, the alkyl group having from 1 to 16 carbon atoms, more preferably from 1 to 5 carbon atoms, and mixtures thereof. The alcohols are more preferably selected from the group consisting of methanol, ethanol, propanol, isopropanol and mixtures thereof; most preferably, the alcohol is methanol.

In all its embodiments, the present invention also incompasses the use of mixtures of alcohol and water selected from the group consisting of technical grade methanol, technical grade ethanol, technical grade propanol, technical grade isopropanol and mixtures thereof, more preferably technical grade methanol.

While the metalloaluminophosphate molecular sieves or metalloaluminophosphate catalyst particles are in contact with the mixture of alcohol and water, it is preferred that the metalloaluminophosphate molecular sieve have a methanol adsorption index of at least 0.5.

Preferably, the metalloaluminophosphate molecular sieve is selected from SAPO-11, SAPO-17, SAPO-18, SAPO-34, SAPO-35, SAPO-37, SAPO-44, SAPO-56, metal containing forms thereof and intergrown forms thereof.

The molecular sieves and catalyst particles of the present invention are useful catalysts for the conversion of hydrocarbons, especially for the conversion of oxygenated feedstocks into derivatives, such as light olefins, more preferably ethylene or propylene, or such as methylamines.

DETAILED DESCRIPTION OF THE INVENTION

1. Introduction

Metalloaluminophosphate, especially SAPO, catalysts are susceptible to catalytic activity and structural changes as a result of continued exposure to even low levels of moisture. We have found that SAPO molecular sieves lose catalytic activity when the catalytic sites are exposed to an open air environment for as little as a few hours after activation, and that loss of catalytic activity is irreversible after a certain point.

The possibility of irreversible loss of catalytic activity presents a problem in the commercial production-to-use chain where storage, handling and transport of the molecular sieve and catalyst can be over a relatively long period of time. For example, the as manufactured molecular sieve can be stored or transported anywhere from 12 hours to many months, even as long as one year, before its final use as an activated catalyst. Even partial loss of catalytic activity is of particular concern in large scale catalytic processes. As defined herein, a large scale catalytic process is one having a catalyst loading in excess of 50 kg, particularly one having a catalyst loading in excess of 500 kg, especially one having a catalyst loading in excess of 5000 kg.

U.S. Pat. No. 6,316,683 (Janssen et al.) discloses a method of protecting catalytic activity of a SAPO molecular sieve under a blanket of anhydrous alcohol, the alcohol having less than about 200 ppm water. We have now surprisingly found that metalloaluminophosphate molecular sieves and catalysts comprising metalloaluminophosphate molecular sieves can be effectively protected from degradation during storage or handling, by contacting the molecular sieve with mixtures of alcohol and water instead of anhydrous alcohol. Such protective effect can be used on fresh catalyst, i.e catalyst that has not yet been used in a catalytic process, or it can be used on a used catalyst, i.e. a catalyst that has been used in a catalytic process, when the used catalyst has to be handled between operation units or during interruptions in reactor operations.

2. Water and Alcohol Mixtures

According to the present invention, metalloaluminophosphate molecular sieves or catalysts comprising metalloaluminophosphate molecular sieves are protected from degradation during aging by contacting the molecular sieves or catalysts with liquid mixtures of alcohol and water.

Suitable alcohol and water mixtures include liquid mixtures of alcohol and water containing from 45 wt % to 99.8 wt % alcohol, preferably from 50 wt % to 99.5 wt %, more preferably from 55 wt % to 99 wt % alcohol, most preferably from 60 wt % to 95 wt % alcohol. Preferably, the alcohol and water mixture contains from 0.2 wt % to 55 wt % water, more preferably from 0.5 wt % to 50 wt % water, even more preferably from 1 wt % to 45 wt %, most preferably from 5 wt % to 40 wt % water.

The water and alcohol mixture may also contain other components in trace amounts, such as other oxygenated compounds (f. ex. ketones, aldehydes, carboxylic acids, carboxylic esters, peroxides, epoxides, ethers) or alkanes.

While any alcohol may be used, preferred alcohols include alkyl alcohols. More preferably, the alcohol is one or several alkyl alcohols in which the alkyl group, which may be linear or branched, has from 1 to 16 carbon atoms, even more preferably from 1 to 9 carbon atoms and most preferably from 1 to 5 carbon atoms. From practical and economic points of view, the alcohol is preferably methanol, ethanol, propanol or isopropanol. Commercially available liquid mixtures of alcohol and water are suitable for the present invention. Examples of commercial liquid mixtures of alcohol and water include crude alcohols, or any other grades of alcohol, which typically contain percentage levels of water. Preferred commercial water and alcohol mixtures include crude methanol, grade A methanol, "MTO" grade methanol, crude ethanol, crude propanol, crude isopropanol or any other grade of these alcohols containing the appropriate level of water. Mixtures of such alcohol/water mixtures are also suitable. Other suitable water and alcohol mixtures include mixtures of alcohols having from 9 to 16 carbon atoms.

When mixing alcohol and water, various grades of water can be used, including demineralized water, boiler feed water or purified process water. The water should not contain more than 0.5 wt percent, preferable not more than 0.1 wt percent, more preferably not more than 0.01 wt percent contaminants.

The mixture of alcohol and water is in the liquid state while contacting the activated metalloaluminophosphate molecular sieve. Such contacting can take place under a variety of temperature and pressure conditions, provided the mixture of alcohol and water is maintained in the liquid state. Contacting typically takes place by immersing or suspending the molecular sieve or catalyst in the alcohol and water mixture, for example in the form of a slurry of particles in the liquid alcohol/water mixture.

If the catalyst is intended for use in a process for the conversion of oxygenates to hydrocarbon products, it is best to choose an alcohol that will not generate new unknown by-products during the conversion process. This way, the water and alcohol mixture used to protect the metalloaluminophosphate molecular sieve does not need to be completely removed or, even, does not need to be removed at all, before the catalyst is loaded into the reactor. Excess water/alcohol can easily be removed from the product streams of the conversion process without any special equipment or additional purification step.

Contacting of the molecular sieve or catalyst with the water and methanol mixture is conveniently performed by using a liquid mixture of alcohol and water having the desired alcohol content, and pouring or pumping it over the molecular sieve or catalyst that needs to be protected, to form a liquid blanket. Alternatively, the molecular sieve or catalyst can be immersed or dumped into a vessel containing the liquid mixture of alcohol and water having the desired alcohol content.

3. Molecular Sieves and Catalysts Thereof

The metalloaluminophosphate molecular sieves which may be used in the present invention have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO4), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554, 143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500, 651, 4,551,236 and 4,605,492 (TiAPO), U.S. Pat. Nos. 4,824, 554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686, 093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other metalloaluminophosphate molecular sieves include those described in EP-0 888 187 B1 (microporous crystalline metalloaluminophosphates (UIO-6)), U.S. Pat. No. 6,004, 898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak, Handbook of Molecular Sieves, Van Nostrand Reinhold, New York, N.Y. (1992), which are all herein fully incorporated by reference.

The most preferred molecular sieves are SAPO molecular sieves, and metal substituted SAPO molecular sieves. In one embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof.

The metalloaluminophosphate molecular sieve may be represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of M, Al and P as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

As used herein, the term mixture is synonymous with combination and is considered a composition of matter having two or more components in varying proportions, regardless of their physical state. In particular, it encompasses physical mixtures as well as intergrowths of at least two different molecular sieve structures; such as for example those described in PCT Publication No. WO 98/15496 and co-pending U.S. Ser. No. 09/924,016 filed Aug. 7, 2001. In an embodiment, the molecular sieve is an intergrowth material having two or more distinct phases of crystalline structures within one molecular sieve composition. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type. In a further embodiment the molecular sieve comprises a mixture of intergrown material and non-intergrown material.

The method of stabilization of the present invention may be utilized with metalloaluminophosphate molecular sieves which are particularly unstable to moisture exposure e.g. morpholine templated SAPO-34 and may also be used to stabilize relatively moisture insensitive molecular sieves such as dual templated (DPA and TEAOH) SAPO-34 materials which may be significantly affected during extended periods of aging or on exposure to water vapor.

Generally, metalloaluminophosphate molecular sieves are synthesized by the hydrothermal crystallization of one or more of a source of aluminum, a source of phosphorous, a source of silicon, a templating agent, and a metal containing compound. Typically, a combination of sources of silicon, aluminum and phosphorous, optionally with one or more templating agents and/or one or more metal containing compounds are placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting. Examples of metalloaluminophosphate molecular sieve synthesis conditions have been described in U.S. Pat. Nos. 4,440,871, 4,861,743, 5,096, 684, and 5,126,308, which are all herein fully incorporated by reference.

Non-limiting examples of templating agents include, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl-(1,6)hexanediamine, N-methyldiethanolamine, N-methylethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2) octane ion; di-n-butylamine, neopentylamine, di-n-pentylamine, isopropylamine, t-butyl-amine, ethylenediamine, pyrrolidine, and 2-imidazolidone. The preferred templating agent or template is a tetraethylammonium compound, such as tetraethyl ammonium hydroxide (TEAOH), tetraethyl ammonium phosphate, tetraethyl ammonium fluoride, tetraethyl ammonium bromide, tetraethyl ammonium chloride and tetraethyl ammonium acetate. In one embodiment, a combination of two or more of any of the above templating agents is used in combination with one or more of a silicon-, aluminum-, and phosphorous-source.

Other suitable metalloaluminophosphate molecular sieves for use in the present invention may be prepared as described in U.S. Pat. No. 5,879,655 (controlling the ratio of the templating agent to phosphorous), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorous modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil), U.S. patent application Ser. No. 09/929,949 filed Aug. 15, 2001 (cooling molecular sieve), U.S. patent application Ser. No. 09/615,526 filed Jul. 13, 2000 (metal impregnation including copper), U.S. patent application Ser. No. 09/672,469 filed Sep. 28, 2000 (conductive microfilter), and U.S. patent application Ser. No. 09/754,812 filed Jan. 4, 2001 (freeze drying the molecular sieve), which are all herein fully incorporated by reference.

In one embodiment, the metalloaluminosphosphate molecular sieve is activated after molecular sieve crystallization. For this purpose, the templating agent is substantially, preferably completely, removed after crystallization by numerous well known techniques, for example, heat treatments such as calcination. Calcination involves contacting the molecular sieve containing the templating agent with a gas, preferably containing oxygen, at any desired concentration at an elevated temperature sufficient to either partially or completely decompose and oxidize the templating agent.

In one embodiment, the molecular sieve has a Si/Al2 ratio less than 0.65, preferably less than 0.40, more preferably less than 0.32, and most preferably less than 0.20.

Once the molecular sieve is synthesized the molecular sieve may then be handled or stored by contacting the molecular sieve with a liquid water/alcohol mixture to prevent water degradation of the molecular sieve. The protected, molecular sieve can then be formulated into a molecular sieve catalyst composition. In another embodiment, the metalloaluminophosphate molecular sieve as synthesized, i.e. without having removed the template (for example in the form of a wet filter cake), may be formulated into a catalyst composition. Activation of the molecular sieve then occurs from within the catalyst composition, once the catalyst composition is heated under conditions that allow partial or complete removal of the template from the molecular sieve pore structure.

Molecular sieve activation thus can occur prior to or after the molecular sieve has been formulated into a catalyst composition. In each of these embodiments, the catalytic sites of the molecular sieve can be protected against water degradation during molecular sieve and/or catalyst handling and/or storage by maintaining the molecular sieve or the catalyst in contact with a liquid mixture of water and alcohol.

In either instance a catalyst composition can be made by combining the metalloaluminophosphate molecular sieve with a binder and/or a matrix material to form a molecular sieve catalyst composition. This catalyst composition is formed into useful shaped and sized particles by well-known techniques such as spray drying, pelletizing, extrusion, and the like. If the molecular sieve has been activated before combining with the binder and/or the matrix material, it is best to handle and store the molecular sieve in contact with a liquid mixture of water and alcohol according to the present invention, for as long as practically possible. The water and alcohol mixture used as protecting agent can be, but does not necessarily need to be, removed before the molecular sieve is combined with the binder and/or matrix material. The water and alcohol mixtures used according to the present invention are suitable mediums for formulating molecular sieves into catalysts. In an embodiment, the activated metalloaluminophosphate molecular sieves can be stored as slurries in the alcohol and water mixtures of the invention after molecular sieve synthesis. The other catalyst formulation agents can then be added to these water and alcohol molecular sieve slurries at the time of catalyst formulation.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p\cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7\cdot 12(H_2O)$ as is described in G. M. Wolterman, et al., Stud. Surf. Sci. and Catal., 76, pages 105-144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The metalloaluminophosphate molecular sieve may be combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry; it has a low fresh surface area, and it packs together easily due to its platelet structure. A preferred average particle size of the matrix material, most preferably kaolin, is from about 0.1 µm to about 0.6 µm with a D90 particle size distribution of less than about 1 µm.

In one embodiment, the binder, the molecular sieve and the matrix material are combined in the presence of a liquid to form a molecular sieve catalyst composition, where the amount of binder is from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid (after calcination).

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

Upon combining the molecular sieve and the matrix material, optionally with a binder, in a liquid to form a slurry, mixing, preferably rigorous mixing is needed to produce a substantially homogeneous mixture containing the molecular sieve. Non-limiting examples of suitable liquids include one or a combination of water, alcohol, ketones, aldehydes, and/or esters. The most preferred liquids are water/alcohol mixtures and water. In one embodiment, the slurry is colloid-milled for a period of time sufficient to produce the desired slurry texture, sub-particle size, and/or sub-particle size distribution. In the present invention the use of a mixture of alcohol and water is beneficial in the catalyst formulation process as the water/alcohol mixture protects the molecular sieve from degradation during the formulation process.

The molecular sieve and matrix material, and the optional binder, may be in the same or different liquid, and may be combined in any order, together, simultaneously, sequentially, or a combination thereof. In one embodiment, the slurry of the molecular sieve, binder and matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is a spray dryer. Typically, the forming unit is maintained at a temperature sufficient to remove most of the liquid from the slurry, and from the resulting molecular sieve catalyst composition. The resulting catalyst composition when formed in this way takes the form of microspheres.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature.

In a preferred embodiment, the molecular sieve catalyst composition is heated in nitrogen at a temperature of from about 600° C. to about 700° C. Heating is carried out for a period of time typically from 30 minutes to 15 hours, preferably from 1 hour to about 10 hours, more preferably from about 1 hour to about 5 hours, and most preferably from about 2 hours to about 4 hours.

Other methods for activating a molecular sieve catalyst composition, are described in, for example, U.S. Pat. No. 5,185,310 (heating molecular sieve of gel alumina and water to 450 C), PCT WO 00/75072 published Dec. 14, 2000 (heating to leave an amount of template), and U.S. application Ser. No. 09/558,774 filed Apr. 26, 2000 and published as PCT Publication No. WO 01/80995 to Janssen et. al (rejuvenation of molecular sieve), which are all herein fully incorporated by reference.

In addition to the metalloaluminophosphate molecular sieve, the catalyst compositions of the present invention may comprise one or several additional catalytically active materials. In one embodiment, one or several metalloaluminophosphate molecular sieves are combined with one more of the following non-limiting examples of catalytically active molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527) MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (EP-A-0 229,-295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345).

In another embodiment, the metalloaluminophosphate may be bound to another molecular sieve, as disclosed for example in the following: SAPO-34 bound ALPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference. Binder may no longer be necessary in such systems.

In a further embodiment, the metalloaluminophosphate molecular sieve may be combined with a metal catalyst, for example as a Fischer-Tropsch catalyst The catalyst compositions of the present invention may comprise one or more metalloaluminophosphate molecular sieves, which may be combined with one or more non-metalloaluminophosphate molecular sieves such as zeolites of zeolite-like molecular sieves described above. It is preferred that the catalyst comprises metalloaluminophosphates as the sole molecular sieve component.

4. Aging Conditions

In the context of the present invention an aged metalloaluminophosphate molecular sieve is either an activated metalloaluminophosphate molecular sieve or an activated metalloaluminophosphate molecular sieve in a formulated catalyst particle, which has been stored for an extended period of time after synthesis, or it is a metalloaluminophosphate molecular sieve material, which has been used in a catalytic process and has been removed from that process or temporarily retained under non-optimum process conditions such as in a shutdown phase. Similarly, in the context of the invention, an aged catalyst composition is an activated catalyst composition as formed, which has been stored for an extended period of time after synthesis, or it is a used catalyst composition, which has been used in a catalytic process and has been removed from that process or temporarily retained under non-optimum process conditions such as in a shutdown phase. By extended periods of time is meant a period greater than 6 hours, preferably greater than 12 hours, more preferably more than 24 hours, even more preferably greater than 36 hours, yet even more preferably greater than 48 hours, and most preferably greater than 72 hours. Preferably, the period of aging in the presence of a water and alcohol mixture does not take place for more than 12 months. The period of aging while in contact with the water and alcohol mixture may be under a variety of temperature and pressure conditions, provided the alcohol/water mixture is in the liquid state.

In addition to contacting the molecular sieve or catalyst with a mixture of water and alcohol, the period of aging can be undertaken under an inert atmosphere, for example in a sealed container such as storage drum or holding facility after manufacture of the sieve or catalyst.

When aged in contact with a liquid mixture of alcohol and water of the present invention, the molecular sieve or molecular sieve-containing catalyst composition is stable. By stable is meant that there is less reduction in the catalytic activity of the molecular sieve maintained in contact with the water and alcohol mixture compared to the same molecular sieve maintained under the same conditions, but without contact with a water and alcohol mixture of the invention. The molecular sieve or catalyst may be maintained in contact with the alcohol/water mixture for an extended period of time, which is typically at least 6 hours, preferably at least 12 hours and which may be for any period of storage, shipping or handling greater than 12 hours.

International Patent Application PCT/US01/43653, published 6 Sep. 2003 as WO 02/068364, discloses a method for converting an oxygenate to an olefin product, using a silicoaluminophosphate molecular sieve that has been contact with an alcohol in an alcohol contact zone prior to the oxygenate to olefin conversion reaction. The present invention differs from many aspects from the process disclosed in WO 02/068364, as the present invention requires that the metalloaluminophosphate molecular sieve be maintained in contact with the mixture of alcohol and water for an extended period of time. In the context of WO 02/068364, contacting the mixture of alcohol and water is performed for shorter periods of time than meant in the present invention. The present invention envisions storing and/or handling the catalyst while being protected with a mixture of alcohol and water, while WO 02/068364 envisions a pre-treatment before catalytic use, to modify the catalytic performance of the metalloaluminophosphate molecular sieve. In WO 02/068364, the alcohol contacts the metalloaluminophosphate molecular sieve continuously at a weight hourly space velocity of from about 1 hr-1 to about 500 hr-1, whereas in the present invention, the mixture of alcohol and water are not fed continuously; in the present invention, a fixed amount of the mixture of alcohol and water is mixed with the molecular sieve or catalyst particles, and remains with the catalyst during the entire duration of the contacting (storage and/or handling) period.

In one embodiment of the present invention, the molecular sieve is contacted with a water/methanol mixture for at least 24 hours, preferably at least 48 hours and most preferably at least 72 hours at ambient conditions. Ideally the molecular sieve or catalyst is held in this state as long as possible before use, provided the methanol uptake index, as defined in this application, of the molecular sieve or catalyst has not dropped below 0.5.

One suitable method for determining catalyst activity and catalyst activity loss over time is to determine the methanol adsorption capacity (MAC) of the molecular sieve or catalyst immediately after activation and to monitor this capacity with time. Ideally the MAC should remain as high as possible up to the point at which the molecular sieve is used in a conversion process. For molecular sieve catalysts, which are activated in situ, i.e. the template is removed on introduction of the molecular sieve to the conversion process, the time between activation and actual contact with feed is short enough such that the initial methanol adsorption capacity is essentially equivalent to the methanol adsorption capacity at feed contact.

At the time of feed contact means the point in time when the activated molecular sieve is contacted with feedstock under conditions effective to convert the feedstock to product, the product containing measurable portions of desired product. This does not imply, however, that the methanol adsorption capacity at the time of catalytic contact with the feedstock must be calculated at the exact instant that feedstock contacts activated molecular sieve. This is because it may not be possible to run such a precise calculation, particularly in evaluating large scale reaction systems. Therefore, the methanol adsorption capacity at feed contact must be evaluated as soon as practical before contact with feed. Under some circumstances, especially when dealing with large scale systems, as close as practical may extend up to as much as 12 hours between activation and actual contact with feed under catalytic conversion conditions.

In the present invention, contacting the molecular sieve with a mixture of alcohol and water is effective in retaining the methanol uptake properties of the molecular sieve, which are higher than those achieved when the molecular sieve is not contacted with the mixture of alcohol and water. It is particularly surprising that mixtures of alcohol containing up to 55 wt % water are susceptible of preventing water damage of the molecular sieves.

The measurement of MAC may be used in the context of the present invention to demonstrate the effective stabilization effect of water/alcohol mixtures of the invention. Contacting the molecular sieve with alcohol and water mixtures results in improved MAC values after aging (i.e. storage, shipping, handling). According to this invention, it is preferred that the MAC after contact with the liquid alcohol/water mixtures is at least 15%, preferably at least 40%, more preferably at least 60%, and most preferably at least 80%, of the original MAC before contacting the molecular sieve with the alcohol and water mixture according to the present invention. Techniques for measuring methanol adsorption capacity are known to those of ordinary skill in the art.

Another way to express the loss of catalytic activity over time, it to calculate the methanol uptake index (MUI) of molecular sieve or catalyst. The MUI is defined as the ratio between the maximum methanol adsorption capacity (wt %) of an activated molecular sieve or catalyst (i.e., the initial methanol adsorption capacity) and the methanol adsorption capacity (wt %) of the activated molecular sieve or catalyst after the molecular sieve or catalyst has been aged for a given period of time. According to this invention, it is preferred that the MUI be at least 0.15, preferably at least 0.4, more preferably at least 0.45 and most preferably at least 0.5, at the time of catalytic contact. Contact with the feed should thus occur before the MUI drops below 0.15.

In the context of the present invention aged metalloaluminophosphates are typically present in large amounts i.e. the bulk state. By bulk state is meant in the form of a large batch of material or catalyst comprising the metalloaluminophosphate. Typically a bulk sample has a batch size of greater than 1 kilogram, preferably greater than 10 kilogram and most preferably greater than 50 kilogram. The aging may be undertaken in the presence of an inert gas in addition to the water and alcohol mixture. In the present invention it is possible to utilize grades of inert gases which were hitherto unacceptable for metalloaluminophosphate molecular sieve storage due to inter alia their moisture content. Such gases may be of lower purity and quality e.g. they may contain higher than normal levels of impurities such as oxygen and/or moisture.

The present invention provides a method of protecting an activated molecular sieve or catalyst from ambient degradation during handling and storage. Handling of an activated molecular sieve or activated catalyst starts to occur after molecular sieve synthesis and calcination. At that moment, it is particularly useful to handle the activated molecular sieve or catalyst in the form of a slurry in an alcohol and water mixture according to this invention. This way, the molecular sieve or catalyst is protected against ambient degradation. Furthermore, for large scale operations, it is very practical and convenient to handle slurries during materials transfer, such as shipping, truck loading, truck unloading and loading into reactor vessels. As water would severely damage catalytic activity during these handling steps, it is very advantageous to be able to use alcohol and water mixtures rather than water to carry out these handling steps.

In another embodiment, water and alcohol mixtures of the invention can be used to protect catalyst from loss of catalytic activity during reactor operation interruptions that require temporary catalyst storage. During conversion processes, it may be necessary to shut the reactor down in either an emergency or in a planned shutdown and maintenance cycle. When this occurs it is often necessary to remove the used catalyst from the reactor and to place the catalyst into temporary storage, which is usually under an inert atmosphere. Sometimes removal is not necessary or desirable and the catalyst is maintained within the plant itself. In both situations the catalyst is under risk of losing its catalytic activity and/or other properties due to aging effects. During such events catalyst can be effectively protected against the effects of water by blanketing with mixtures of alcohol and water. In this embodiment the used catalyst may be treated with a liquid mixture of alcohol and water as it is removed from the plant; the water/alcohol mixture can be maintained in contact with the catalyst as it is re-introduced to the plant. In an alternative embodiment the used catalyst is treated within the plant during or after shutdown.

After the aging period is over, it may be desirable to separate the metalloaluminophosphate molecular sieve from contact with the alcohol and water mixture. This can be achieved by any method, for example, filtration, centrifugation, decanting, drying, calcination, or any combination of these steps.

5. Using the Molecular Sieve Catalyst Compositions

The molecular sieve catalysts and compositions of the present invention are useful in a variety of processes including: cracking, hydrocracking, isomerization, polymerization, reforming; hydrogenation, dehydrogenation, dewaxing, hydrodewaxing, absorption, alkylation, transalkylation, dealkylation, hydrodecylization, disproportionation, oligomerization, dehydrocyclization and combinations thereof.

The preferred processes of the present invention include a process directed to the conversion of a feedstock comprising one or more oxygenates to one or more derivative products, such as methylamines or olefins, most preferably olefin(s).

Prior to being used in these processes, the water and alcohol mixture used to protect the molecular sieve from ambient degradation can be removed if desired. However, for catalytic processes using oxygenated feedstocks, the water and alcohol mixture does not necessarily need to be removed before loading into the reactor, or even before contacting with the oxygenated feedstock begins.

In a preferred embodiment of the process of the invention, the feedstock comprises one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The protected metalloaluminophosphate molecular sieves of the present invention are suitable for use as catalysts in a variety of hydrocarbon conversion processes, including aromatic alkylation, the manufacture of methylamines and the manufacture of olefins. For aromatic alkylation, the feedstock comprises at least one oxygenated hydrocarbon and at least one aromatic hydrocarbon; for methylamine manufacture, the feedstock comprises at least one oxygenated hydrocarbon and ammonia; for the manufacture of olefin(s), the feedstock comprises at least one oxygenated hydrocarbon.

In a preferred embodiment, the feedstock, preferably of one or more oxygenates, is converted in the presence of a molecular sieve catalyst composition into olefin(s) having 2 to 6 carbons atoms, preferably 2 to 4 carbon atoms. More preferably, the olefin(s), alone or combination, are converted from a feedstock containing an oxygenate, preferably an alcohol, most preferably methanol, to the preferred olefin(s) ethylene and/or propylene.

The most preferred process is generally referred to as gas-to-olefins (GTO) or alternatively, methanol-to-olefins (MTO). In a MTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

The feedstock can contain one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. The diluent, water, is used either in a liquid or a vapor form, or a combination thereof. The diluent is either added directly to a feedstock entering into a reactor or added directly into a reactor, or added with a molecular sieve catalyst composition.

In a preferred embodiment of this invention, feedstock used for the GTO process is used as the alcohol and water mixture that contacts the molecular sieve during catalyst handling and storage.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and Fluidization Engineering, D. Kunii and O. Levenspiel, Robert E. Krieger Publishing Company, New York, N.Y. 1977, which are all herein fully incorporated by reference.

The preferred reactor type are riser reactors generally described in Riser Reactor, Fluidization and Fluid-Particle Systems, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel; typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 hr-1 to about 20,000 hr-1 based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 hr-1 to about 5000 hr-1, preferably from about 2 hr-1 to about 3000 hr-1, more preferably from about 5 hr-1 to about 1500 hr-1, and most preferably from about 10 hr-1 to about 1000 hr-1. In one preferred embodiment, the WHSV is greater than 20 hr-1; preferably the WHSV for conversion of a feedstock containing methanol and dimethyl ether is in the range of from about 20 hr-1 to about 300 hr-1.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

During catalyst use, the catalyst becomes coked. The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

In an embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The regenerated molecular sieve catalyst composition withdrawn from the regeneration system is combined with a fresh molecular sieve catalyst composition and/or re-circulated molecular sieve catalyst composition and/or feedstock and/or fresh gas or liquids, and returned to the riser reactor(s). In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

By controlling the flow of the regenerated molecular sieve catalyst composition or cooled regenerated molecular sieve catalyst composition from the regeneration system to the reactor system, the optimum level of coke on the molecular sieve catalyst composition entering the reactor is maintained. There are many techniques for controlling the flow of a molecular sieve catalyst composition described in Michael Louge, Experimental Techniques, Circulating Fluidized Beds, Grace, Avidan and Knowlton, eds. Blackie, 1997 (336-337), which is herein incorporated by reference.

The gaseous effluent is withdrawn from the disengaging system and is passed through a recovery system. There are many well-known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like.

In order to provide a better understanding of the present invention including representative advantages thereof, the following examples are offered.

6. EXAMPLES

SAPO-34 was prepared according to the following procedure: 80.1. g of alumina (Pural SB Condea 75%) was mixed with 422.3 g of deionised water to form a slurry. To this slurry was added 135.61 g of phosphoric acid (85%) with stirring to form a homogeneous mixture. To this homogeneous mixture was added 53.1 g of colloidal silica (Ludox AS40), followed by the addition of 157.4 g of morpholine (98%) with mixing to form a homogeneous mixture. To this homogenized mixture was added 2.0 g of CHA seeds. This resulted in an overall seed concentration in the mixture of 206 wt ppm. The molar composition of the mixture was:

$Al_2O_3:P_2O_5:0.6\ SiO_2:3\ Morpholine:50\ H_2O+206$ wt ppm CHA seeds

The mixture was placed in a 1 liter stainless steel autoclave, heated up to 175° C. in 8 hours without stirring and kept at that temperature for 48 hours. The resultant slurry of crystalline material was washed and dried overnight at 120° C. The yield of dried SAPO-34 material, expressed as a wt % on the total initial synthesis slurry, was 16.5%.

This SAPO-34 was calcined for 5 hours under nitrogen, followed by 3 hours under air at 650° C. to remove the organic templating agent (morpholine). This sample shall be hereinafter referred to as "freshly calcined SAPO-34".

A portion of the freshly calcined SAPO was stored under water, while other portions of the freshly calcined SAPO were stored under water/methanol mixtures of varying water content. After storage for a given amount of time, the SAPO-34 powders were dried at 60° C. for 10 minutes before determining their methanol adsorption capacity.

The methanol adsorption capacity of the freshly calcined SAPO-34 and of the SAPO-34 samples stored under the various studied conditions was determined as follows:

Each SAPO-34 powder sample was transferred into a TA Instruments SDT 2960 Simultaneous DSC/TGA gravimetric adsorption apparatus. After activation of the SAPO-34 in air at 650° C. for 60 minutes, (20° C./min from ambient to 150° C.; 30 minutes isothermal at 150° C.; 20° C./min from 150° C. to 650° C.), the sample was cooled to 30° C. under a flow of Helium, and methanol vapor was allowed into the system at 30° C. The methanol adsorption capacity (MAC) is the amount of methanol adsorbed when the system is in equilibrium and is given as the increase in weight (in %) of a dehydrated SAPO-34 after methanol uptake.

The methanol uptake index (MUI) is defined as the ratio of the measured methanol adsorption capacity after storage and the methanol adsorption capacity of the freshly calcined SAPO-34. The results are summarized in Table 1.

TABLE 1

| Blanket composition | Methanol uptake index Storage time (hours) | | | | | |
|---|---|---|---|---|---|---|
| Water % in methanol | 0 | 3.75 | 7.75 | 25 | 36 | 60 |
| 100 (pure water) | 1.00 | 0.55 | 0.45 | 0.39 | n.d.* | n.d.* |
| 50 | 1.00 | 0.68 | 0.61 | 0.69 | 0.63 | 0.69 |
| 25 | 1.00 | 0.81 | 0.91 | 0.91 | 0.92 | 0.89 |
| 15 | 1.00 | 0.96 | 0.98 | n.d.* | 0.74 | n.d.* |
| 5 | 1.00 | 0.98 | 0.96 | n.d.* | 0.87 | n.d.* |

*n.d. = not determined

From Table 1, it is clear that activated SAPO-34 can be maintained in contact with liquid methanol/water mixtures for long periods of time while maintaining a MUI largely above 0.15.

The invention claimed is:

1. A method for converting a feedstock into a hydrocarbon product in which a metalloaluminophosphate molecular sieve having a methanol adsorption index of at least 0.15 is contacted with an oxygenated feedstock under oxygenate to olefins conversion conditions, wherein, prior to contacting said feedstock, said metalloaluminophosphate molecular sieve has been aged in activated form while in contact with a fixed amount of a liquid mixture of alcohol and water, the mixture of alcohol and water containing from 45 wt % to 99.8 wt % alcohol and from 0.2 wt %. to 55 wt % water.

2. The method of claim 1, wherein the metalloaluminophosphate molecular sieve which is contacted with the oxygenated feedstock has a methanol adsorption index of at least 0.5.

3. The method of claim 1, wherein the mixture of alcohol and water contains from 50 wt % to 99.5 wt % alcohol.

4. The method of claim 1, wherein the mixture of alcohol and water contains from 55 wt % to 99 wt % alcohol.

5. The method of claim 1, wherein the mixture of alcohol and water contains from 0.5 wt % to 50 wt % water.

6. The method of claim 1, wherein the alcohol in said alcohol and water mixture is selected from the group consisting of alkyl alcohols, the alkyl group having from 1 to 16 carbon atoms, and mixtures thereof.

7. The method of claim 6, wherein the alkyl group has from 1 to 5 carbon atoms.

8. The method of claim 7, wherein the alcohol is selected from the group consisting of methanol, ethanol, propanol, isopropanol and mixtures thereof.

9. The method of claim 1, wherein the mixture of alcohol and water is selected from the group consisting of crude methanol, grade A methanol, crude ethanol, crude propanol, crude isopropanol and mixtures thereof.

10. The method of claim 9, wherein the mixture of alcohol and water is crude methanol.

11. The method of claim 1, wherein aging includes the period of storing the activated metalloaluminophosphate molecular sieve before catalytic use.

12. The method of claim 1, wherein the oxygenated feedstock that contacts the molecular sieve comprises an alcohol selected from the group consisting of methanol, ethanol, propanol, isopropanol and mixtures thereof.

13. The method of claim 12, wherein the oxygenated feedstock that contacts the molecular sieve further comprises water.

14. The method of claim 12, wherein the oxygenated feedstock that contacts the molecular sieve further comprises ammonia.

15. The method of claim 14, wherein the hydrocarbon product comprises methylamines.

16. The method of claim 12, wherein the oxygenated feedstock that contacts the metalloaluminophosphate molecular sieve comprises a mixture of alcohol and water of the same composition as the mixture of alcohol and water that contacts the metalloaluminophosphate molecular sieve while it is aged.

17. The method of claim 16, wherein the oxygenated feedstock comprises technical grade methanol and the liquid mixture of alcohol and water which contacts the metalloaluminophosphate molecular sieve while it is aged also comprises technical grade methanol.

18. The method of claim 1, wherein said hydrocarbon product is one or more olefins.

19. The method of claim 18, wherein said one or more olefins include ethylene and propylene.

20. The method of claim 18, further comprising the step of converting the one or more olefins to a polyolefin.

21. The method of claim 1, further comprising the step of removing the mixture of alcohol and water before contacting the molecular sieve with the oxygenated feedstock under feedstock to hydrocarbon product conversion conditions.

22. The method of claim 21, further comprising the step of calcining the molecular sieve before contacting the molecular sieve with the oxygenated feedstock.

* * * * *